United States Patent
Hornung et al.

(10) Patent No.: US 6,407,964 B1
(45) Date of Patent: Jun. 18, 2002

(54) DEVICE FOR EXAMINING SHEET-LIKE ARTICLES USING ULTRASOUND

(75) Inventors: Heinz Hornung, Gilching; Ulrich Schanda, Holzkirchen, both of (DE)

(73) Assignee: Giesecke & Devrient GmbH, Munich (DE)

( * ) Notice: Subject to any disclaimer, the term of this patent is extended or adjusted under 35 U.S.C. 154(b) by 0 days.

(21) Appl. No.: 09/554,104

(22) PCT Filed: Sep. 27, 1999

(86) PCT No.: PCT/EP99/07164

§ 371 (c)(1),
(2), (4) Date: Jul. 28, 2000

(87) PCT Pub. No.: WO00/19191

PCT Pub. Date: Apr. 6, 2000

(30) Foreign Application Priority Data

Sep. 28, 1998 (DE) .......................... 198 44 447

(51) Int. Cl.[7] .............................. G01N 29/08
(52) U.S. Cl. ..................................... 367/138
(58) Field of Search ................ 367/138, 137, 367/188; 73/597, 159

(56) References Cited

U.S. PATENT DOCUMENTS 4,446,735 A * 5/1984 Weilacher .................. 73/597
4,612,807 A * 9/1986 Wunderer .................. 73/159
5,661,243 A * 8/1997 Bryan et al. ............... 73/597
5,691,474 A * 11/1997 Gerz .......................... 73/159
5,922,960 A * 7/1999 Toda .......................... 73/597

FOREIGN PATENT DOCUMENTS

GB 001323844 A * 7/1973

* cited by examiner

Primary Examiner—Daniel T. Pihulic
(74) Attorney, Agent, or Firm—Bacon & Thomas, PLLC

(57) ABSTRACT

The invention relates to an apparatus for testing sheet material, in particular bank notes, comprising a device for transporting the sheet material in a defined direction, at least one transducer pair with a transmitter which exposes the sheet material to soundwaves and a receiver which detects the sound fraction transmitted through the sheet material, transmitter and receiver being disposed obliquely to each other with respect to the transport plane.

The inventive apparatus is characterized in that the soundwaves emitted by a transducer are passed into a transport channel in which the sheet material to be tested is moved during irradiation, the sound fraction reflected by the sheet material being limited in its propagation by the transport channel such that said sound fraction cannot reach the receiver during irradiation of the sheet material.

15 Claims, 2 Drawing Sheets

DEVICE FOR EXAMINING SHEET-LIKE ARTICLES USING ULTRASOUND

BACKGROUND OF THE INVENTION

This invention relates to an apparatus for testing sheet material, in particular bank notes, comprising a device for transporting the sheet material in a defined direction, at least one pair of transducers with a transmitter which exposes the sheet material to soundwaves and a receiver which detects the sound fraction transmitted through the sheet material, transmitter and receiver being disposed obliquely to each other with respect to the transport plane.

An apparatus of the abovementioned kind is known e.g. from EP 0 167 010 A2. A sound transmitter emits ultrasonic waves onto the moving sheet material, the sound fraction transmitted through the material under test being detected by a receiver. The detected sound intensity is evaluated as a measure for determining the thickness and/or weight per unit area of the sheet material. Transmitter, material under test and receiver are disposed obliquely to each other such that the sound fractions reflected on said elements are directed out of the beam path between transmitter and receiver (measuring path). Additional devices, such as sound traps or sound mirrors, ensure that the removed sound fractions cannot return to the measuring path. However, the use of such additional devices is relatively elaborate and requires additional room.

SUMMARY OF THE INVENTION

The invention is based on the problem of proposing an apparatus for testing sheet material that permits a good signal yield with low technical effort and is of compact construction. This problem is solved according to the invention by the features stated in the characterizing parts of the independent claims.

The basic idea of the invention is that the soundwaves emitted by a transducer are passed into a transport channel in which the sheet material to be tested is moved during acoustic irradiation, second sound fraction of sound waves reflected by the sheet material being limited in its propagation by the transport channel such that said second sound fraction are directed away from the receiver during irradiation of the sheet material. Preferably, the transducer produces a sound lobe with a small aperture angle, the soundwaves emitted by the transducer not impinging directly on the sound-reflecting inner surfaces of the transport channel. Provision of a transport channel avoids interference in the measuring signal by reason of vagrant soundwaves which are not to contribute to measurement. The transport channel permits this to be attained with low technical effort since no additional devices such as sound traps or sound mirrors are required. Further, since the transport plane is free from sound-absorbent materials the transport channel can be made so narrow that the transmitter and receiver can be disposed relatively close together. Since a major part of the soundwaves emitted by the transmitter is reflected by the material under test and only a small part (in the range of a few percent) passes through the material under test in a transmission measurement, the signal yield of the measurement is improved by the small distance between transmitter and receiver. This increases the signal-to-noise ratio when background noise is constant, thereby facilitating evaluation of the measuring signal.

Preferably, testing is effected over the total width of the sheet material, the sheet material moved in the longitudinal direction being scanned in a plurality of measuring tracks perpendicular to the transport direction. This makes it possible e.g. to ascertain adhesive tape on bank notes or tears or holes in the bank notes or else concertina folds or dog ears, which is important for testing the state of bank notes. With a multitrack testing apparatus the transducer pairs (transmitter and receiver) are disposed at a great distance apart in comparison with the distance between the inner surfaces, i.e. the height of the transport channel. The distance between the inner surfaces of the transport channel is preferably selected so that the sound fraction reflected by the sheet material is reflected several times between an inner surface of the channel and the material, the sound intensity decreasing greatly with an increasing number of reflections, thereby making the power of the sound fraction which can pass into an adjacent measuring track negligible. Since this condition depends on many factors, for example the surface quality of the inner surfaces of the transport channel, the maximum angle of emergence of the sound or the reflection factor of the sound-absorbent material, this condition can only be stated as a guideline, whereby the distance between two adjacent measuring tracks should be at least five times as great as the transport channel height.

The transducer is held in position in the housing by an elastic element such that the oscillating body when suitably excited undergoes almost no attenuation through the mounting of the housing and the sound axis of the transmitter is nevertheless aligned exactly with the receiver. One can thus achieve a sufficient signal yield even using small transducers with lower sound power. With multitrack testing of the sheet material, the transducers are preferably disposed on a common elastic element made e.g. of a foam material. For example the elastic element is disposed on the side facing away from the transducers on a board, the connections of the transducers being connected with the board via electric conductors guided e.g. through the foam material. The transducers are surrounded by a housing which defines the positions of the transducers, the housing being connected detachably with the board. This permits the ultrasonic transducers to be replaced in simple fashion, thereby improving ease of maintenance.

BRIEF DESCRIPTION OF THE DRAWINGS

Further advantages and developments of the invention will result from the dependent claims as well as the following description and embodiments of the invention with reference to the enclosed figures, in which:

DETAILED DESCRIPTION OF THE PREFERRED EMBODIMENTS

Figure 1:
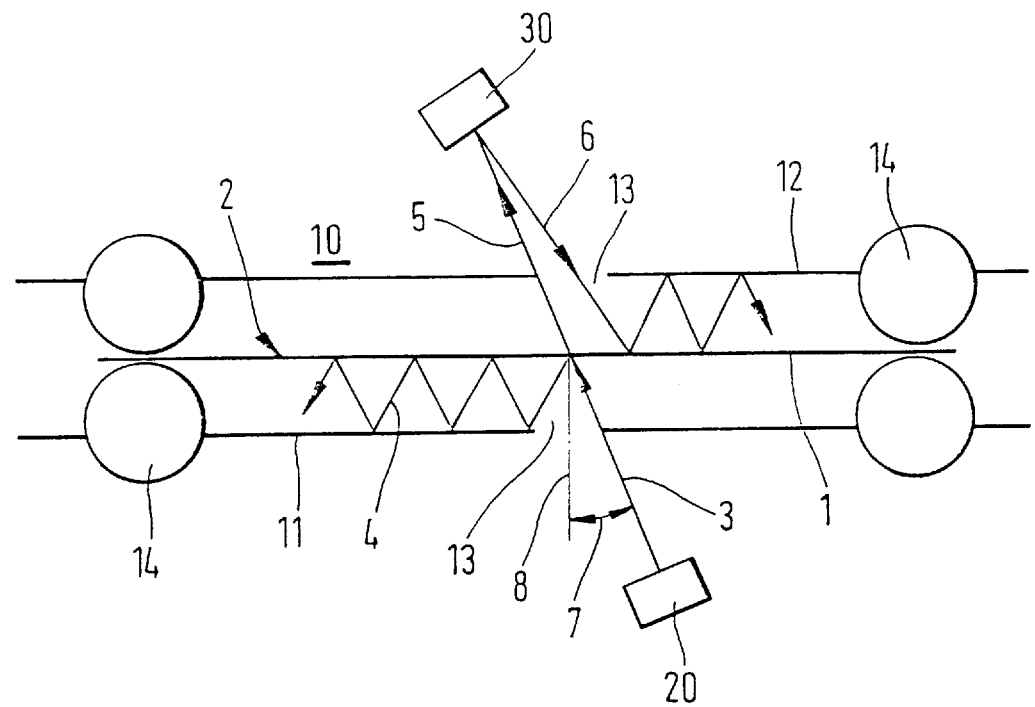
FIG. 1 shows the functional principle of an apparatus for testing sheet material.

FIG. 1 shows by way of example a schematic view of the functional principle of the inventive apparatus. Sheet material 1, e.g. a bank note, is moved by indicated conveyor rollers 14 within transport channel 10 in defined direction 2 between transmitter 20 and receiver 30 disposed below and above the transport channel, respectively. Transmitter and receive are disposed relative to the transport channel such that the soundwaves emitted by the transmitter in the direction of arrow 3 impinge on sheet material 1 through opening 13 in the transport channel at nonzero angle 7 based on perpendicular 8 at the impingement point of the transmitter sound. Transmitter 20 can be operated for example at an operating frequency in the range of 150–250 kHz preferably at the resonance frequency. Operation in the resonance region permits high sound power with a narrow frequency spectrum to be obtained, which is advantageous in transmission measurement. A fraction 4 of the transmitter sound reflected by the sheet material impinges on inner surface 11 of the transport channel in accordance with the reflection condition (angle of incidence=angle of reflection), where it is reflected and again impinges on the sheet material. This second sound fraction 4 is thus reflected several times in controlled fashion between inner surface 11 of the transport channel and the sheet material. At each reflection second sound fraction 4 is scattered so that the intensity of the second sound fraction 4 decreases greatly with an increasing number of reflections and thus becomes negligible. Second sound fraction 4 thus does not disturb the transmission measurement. For testing the sheet material, for example with respect to thickness and/or weight per unit area, a first sound fraction 5 transmitted through the sheet material is detected by receiver 30 and evaluated by a device not shown. For illustration, receive 30 is inclined in FIG. 1 relative to the direction of first sound fraction 5 such that a third sound fraction 6 reflected on the receiver has a different direction from second sound fraction 5. Third sound fraction 6 reflected by the receiver impinges on the sheet material and is reflected thereby in accordance with the reflection condition (angle of incidence=angle of reflection), so that third sound fraction 6 impinges on inner surface 12 of the transport channel and is reflected several times between said inner surface and the sheet material, as described above in connection with second sound fraction 4. Due to the transport channel second and third sound fractions 4, 6 cannot reach the receiver. Furthermore, the transport channel provides a shield so that interference from outside the testing apparatus can have no appreciable influence on the test. Third sound fraction 6 can be neglected, however, unlike second sound fraction 4, by reason of the low transmission factor with sheet material, being for example in the range of a few percent. By reason of the low transmission factor of the sheet material (the sheet material reduces the sound level detected by the receiver and emitted by the transmitter by 40 dB for example), transmitter and receiver can also be disposed parallel to each other without falsifying the measuring result.

Figure 2:
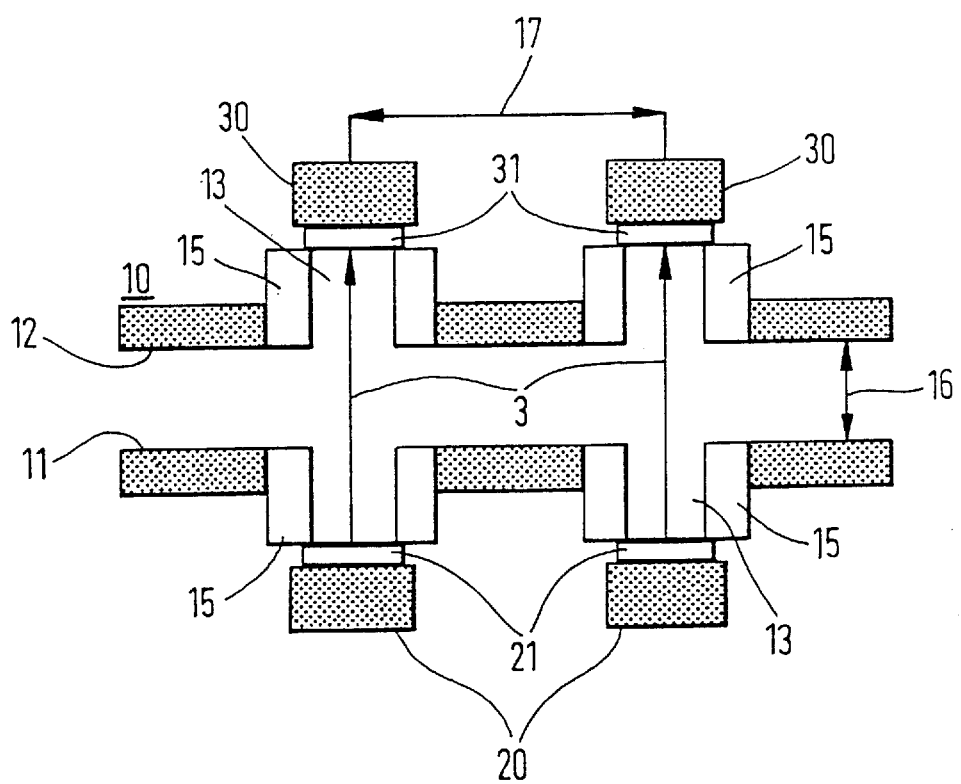
FIG. 2 shows an embodiment of an apparatus with a plurality of measuring tracks.

FIG. 2 shows an apparatus with a plurality of transmitters 20 and receivers 30 disposed along transport channel 10 perpendicular to the transport direction not shown here. Transmitters 20 all have the same radiation characteristic and are otherwise the same as well. This also applies accordingly to receivers 30. Left transmitter 20 with opposite receiver 30 forms the first transducer pair of a first measuring track. Two measuring tracks are shown here by way of example but three or four or even more measuring tracks can of course also be provided. This is dependent on the room available for the testing apparatus and the dimensions of the sheet material. The detecting areas of the testing apparatus defined by the measuring tracks are obviously to be selected with respect to the sheet material such that multiple pulls, adhesive tape on the sheet material, concertina folds or tears in the sheet material are recognized. On the faces of transducers 20, 30 facing openings 13 of transport channel 10, layers 21 and 31 are provided, respectively. Layers 21, 31 consist e.g. of a deadening material and are optional and serve to additionally attenuate any standing soundwaves that might form. The oscillating body can be e.g. a piezoceramic body which is electrically excited to oscillate ultrasonically by a circuit not shown here. Sound 3 is emitted substantially only on the side of layer 21. With a multitrack testing apparatus the dimensions of the transducers are to be selected as small as possible while ensuring a sufficient signal yield or sensitivity of measurement. The dimensions of the transducers are generally given by operating frequency and material of the transducers. The dimensions of the ultrasonic transducer also determine the size and shape of the sound-radiating surface of the transducer, whereby the latter as well as the effective geometric dimensions of the sound channel substantially define the aperture angle of the sound lobe produced. The aperture angle of sound 3 emitted by transmitter 20 should if possible be selected so small that only direct sound 3 emitted in a narrow lobe reaches receiver 30. Sound-carrying openings 13 of transport channel 10 can be made of the same material as the transport channel, for example by the openings being simply milled or drilled into the transport channel. Additionally the walls of openings 13 can be provided with deadening material 15. This causes reflections on the walls of the openings to be suppressed. Provision of deadening material 15 is not obligatory, but dependent on the aperture angle of the sound lobe emitted by the transmitter and the thickness of limiting surfaces 11 and 12 and distance 16 between the limiting surfaces. Since the sensitivity or signal yield of measurement decreases with increasing distance between transmitter and receiver in particular with transmission measurement, distance 16 between limiting surfaces 11 and 12 of transport channel 10 is to be selected as small as possible while still ensuring troublefree transport of the sheet material within the transport channel. Of course, distance 16 between the limiting surfaces is dependent on the thickness of the sheet material to be tested. For testing bank notes this distance can be for example 1 mm to 5 mm. The narrow design of the transport channel causes the sound fraction reflected by the sheet material to be reflected very often between inner surface 11 of the transport channel and the material to be tested not shown here. At each reflection this sound fraction remaining in the transport channel is scattered, so that the intensity of the sound decreases with the number of reflections. The sound power of the sound fraction which can pass from one measuring track to the other measuring track is thus negligible with respect to the measuring result and can therefore not falsify the measuring result. To achieve an optimum result, distance 17 between the transducer pairs or measuring tracks should be great compared to height 16 of the transport channel, the distance between two adjacent tracks being for example at least five times as great as the height of the transport channel.

Figure 3A:
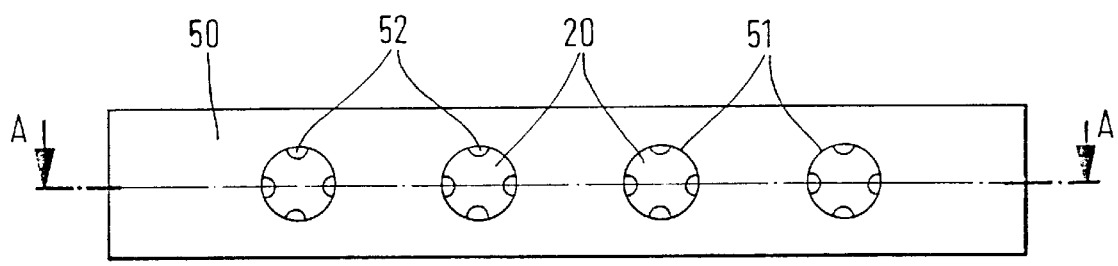
FIGS. 3a, 3b show an embodiment of a transmitter assembly.

FIGS. 3a, b show an embodiment of an inventive ultrasonic transducer assembly as can be used in connection with the sheet material testing apparatus described in FIGS. 1 and 2. FIG. 3a shows a plan view of an embodiment of a transducer assembly with housing 50 having insets 51 or cavities open toward a planar surface defined by an outer periphery of the housing for receiving transduces 20. Each transducer is fixed in position by corresponding knobs 52.

Figure 3B:
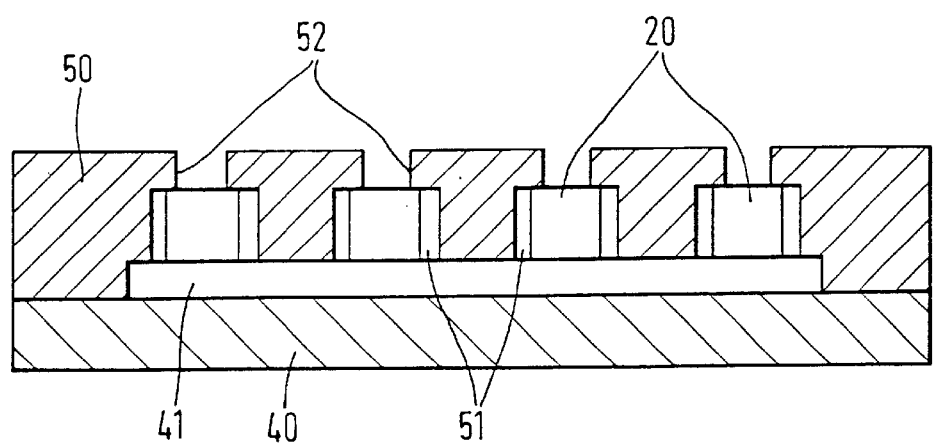

FIG. 3b shows the transducer assembly in a sectional view. Cutting line A—A is shown in FIG. 3a. Housing 50 is connected detachably with board 40 via a snap not shown here. The ultrasonic transducer assembly comprises a plurality of transducers 20 disposed side by side preferably equidistantly. In the embodiment shown here, e.g. four transmitters are disposed on common elastic element 41. Element 41 can be made for example of foam disposed on board 40. Of course, each transmitter 20 can also be disposed on single elastic element 41, e.g. a spring. In both cases the transducers are disposed on the elastic element on the side of the transducer opposite the sound-emitting or sound-receiving side. The sound-emitting side of transducers 20 can additionally be provided with a deadening layer not shown here. Said layer is optional and serves to avoid standing waves. Transducers 20 are positioned between fastening knobs 52 and elastic element 41 such that the sound axes of the transmitters are aligned exactly with the receivers not shown here. Cavity 51 is left on the side walls of the transducers. The cavity has the form of a hollow cylinder whose diameter is greater than the diameter of the transducer. This has the advantage that transducers 20 undergo no appreciable attenuation through the mounting during operation since the transducers are held so as to oscillate almost freely with a force corresponding for example to five times the weight of the transducer. The inventive mounting of the transducers permits the sound power emitted by the transducers in the resonance region to be reduced only negligibly. One can thus achieve a good signal yield even in transmission measurement with small transducers.

What is claimed is:

1. An apparatus for testing the fitness of a sheet material comprising:

a sheet transport device arranged to transport a sheet material in a predetermined direction defining a transport plane, said transport device including a transport channel having parallel sound reflecting surfaces spaced from one another to permit passage of the sheet material therebetween, said transport channel defining openings along each of said sound reflecting surfaces;

at least one transducer pair including:

(a) a transmitter positioned outside of said transport channel along one of said reflecting surfaces near one of said openings formed along thereof, and arranged to emit sound waves directed through said one opening at said sheet material;

(b) a receiver positioned outside of said transport channel along another of said reflecting surfaces near another of said openings formed along thereof, and arranged to detect a first sound fraction of the sound waves, said first sound fraction constituting said sound waves transmitted through the sheet material and said another opening towards said receiver;

wherein a second sound fraction of said sound waves is reflected by said sheet material and limited in propagation by at least one of said reflecting surfaces such that said second sound fraction is directed away in said transport channel from impinging said receiver.

2. The apparatus according to claim 1 wherein said transmitter emits said sound waves at a low aperture angle such that said sound waves are directed away from impinging said reflecting surfaces.

3. The apparatus according to claim 1 wherein said transport device includes conveyor rollers extending into the transport channel and configured to transport said sheet material through said channel.

4. The apparatus according to claim 1 wherein a plurality of transducer pairs are arranged along said transport channel adjacently spaced from one another and perpendicular to said transport plane, each transducer pair defining a measuring track.

5. The apparatus according to claim 4 wherein a distance defined between said adjacent transducer pairs is greater than a distance defined between said reflecting surfaces, said transport channel dimensioned and configured such that said second sound fraction produced by sound waves of a first measuring track being successively reflected within said transport channel and diminished in intensity while traveling along said transport channel so as to become negligible to measuring tracks adjacent to said first measuring track.

6. The apparatus according to claim 5 wherein said distance between said reflecting surfaces is approximately between 1 mm to 5 mm.

7. The apparatus according to claim 6 wherein the distance between each of said adjacent transducer pairs is at least five times greater than the distance between said reflecting surfaces.

8. An ultrasonic transducer assembly for the apparatus according to claim 1 comprising at least one transducer having a sound emitting side and a sound receiving side, said transducer positioned along either the sound emitting side or the sound receiving side on an elastic element and surrounded by a housing securing said transducer in a predetermined position.

9. The ultrasonic transducer assembly according to claim 8 wherein said housing defines at least one cavity configured and dimensioned to receive said at least one transducer and accommodate a plurality of knobs arranged to cooperate with said housing to secure said transducer in said predetermined position.

10. The ultrasonic transducer assembly according to claim 9 wherein said cavity extends into said housing from a planar surface defined by the periphery of said housing and has a cylindrical shape with a diameter greater than a diameter of the transducer positioned therein, said knobs arranged to protrude into said cavity from said planar surface.

11. The ultrasonic transducer assembly according to claim 8 further comprising a board wherein said elastic element is positioned thereon and electrical connections of the transducer electrically couple with said board.

12. The ultrasonic transducer assembly according to claim 11 wherein said housing detachably connects to said board.

13. The ultrasonic transducer assembly according to claim 8 wherein a plurality of said transducers are positioned side-by-side at a predetermined distance from one another and secured by said housing.

14. The ultrasonic transducer assembly according to claim 13 wherein said transducers are secured by a common elastic element.

15. The ultrasonic transducer assembly according to claim 13 wherein said transducers are each secured by an individual elastic element.

* * * * *